Figure 1:
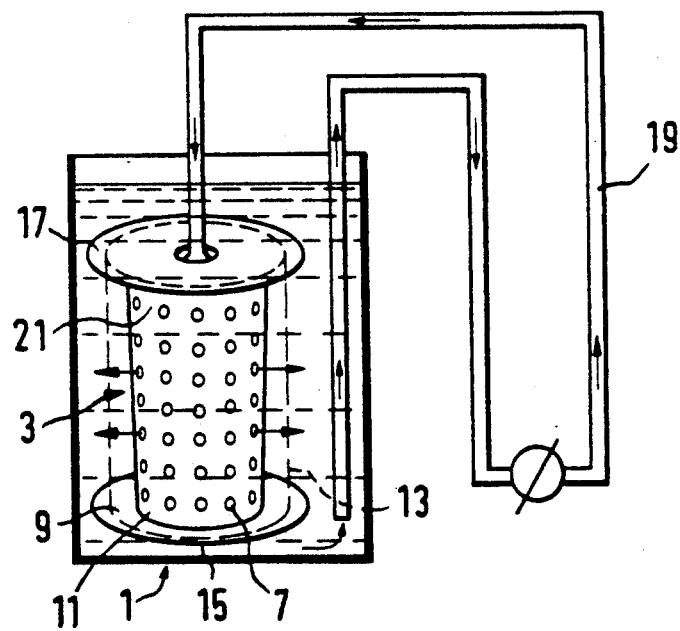

United States Patent [19]

Mang

[11] Patent Number: 5,045,535
[45] Date of Patent: Sep. 3, 1991

[54] METHOD, APPARATUS AND A COMPOSITION FOR A POLYSACCHARIDE-CONTAINING MATRIX HAVING COVALENTLY BOUND HAPTENS

[75] Inventor: Thomas Mang, Penzberg, Fed. Rep. of Germany

[73] Assignee: Boehringer Mannheim GmbH, Mannheim-Waldhof, Fed. Rep. of Germany

[21] Appl. No.: 282,374

[22] Filed: Dec. 9, 1988

[30] Foreign Application Priority Data

Dec. 24, 1987 [DE] Fed. Rep. of Germany ....... 3744068

[51] Int. Cl.$^5$ .................. C08B 1/10; C08B 1/12; C08B 15/06
[52] U.S. Cl. ..................... 514/57; 435/7.1; 435/7.5; 530/810; 530/813; 530/814; 436/529; 436/530; 354/297; 536/124
[58] Field of Search ............... 435/7; 530/810, 813, 530/814; 436/529, 530; 514/57; 536/124

[56] References Cited

U.S. PATENT DOCUMENTS

| | | | |
|---|---|---|---|
| 2,609,368 | 9/1952 | Gaver | 536/121 |
| 3,819,610 | 6/1974 | Akin | 530/810 |
| 4,894,229 | 1/1990 | Polson et al. | 530/810 |

FOREIGN PATENT DOCUMENTS 60-169500 9/1985 Japan.

OTHER PUBLICATIONS

Patent Abstracts of Japan (Dec. 2, 1987), vol. 11, No. 369, p. 134, Appl. No. 62-142122.

*Primary Examiner*—Ronald W. Griffin
*Attorney, Agent, or Firm*—Felfe & Lynch

[57] ABSTRACT

The present invention provides a process for the production of a polysaccharide matrix to which haptens are covalently bound, wherein polysaccharide-containing material is rendered alkaline, dried to a water content of less than 5% and then reacted in an anhydrous medium with a hapten containing at least one activated functional group.

The present invention also provides a device for carrying out this process, which comprises a winding core (3) in a container (1) for a reaction solution which has a tube (11), provided on its wall with a plurality of openings (7) and closed on one end (9), for the reception of a winding (13) of the material to be treated and two axial end walls (15, 17) for sealing off the axial ends of the winding (13) and feeds the reaction solution from the container (1) into the other end (21) of the tube (11) by means of a circulating pump cycle (19).

12 Claims, 2 Drawing Sheets

METHOD, APPARATUS AND A COMPOSITION FOR A POLYSACCHARIDE-CONTAINING MATRIX HAVING COVALENTLY BOUND HAPTENS

The present invention is concerned with a process for the production of a polysaccharide-containing matrix to which haptens are covalently bound, as well as a device suitable therefor.

Carrier materials to which haptens are adsorptively or covalently bound are used not only in the carrying out of immunological detection processes according to the immunoassay principle but also for affinity chromatography. For this purpose, it is necessary that the binding of the haptens to the matrix is so strong that they are not dissolved off under the conditions used in affinity chromatography or in carrying out an immunoassay.

In the case of affinity chromatography, haptens are bound to a carrier in order specifically to separate off with this hapten specifically bindable substances, for example antibodies directed against the hapten, from a mixture. After separation of the mixture, for example in a chromatography column, the bound specifically bindable substance must again be eluted from the hapten. However, the hapten must thereby not be dissolved off.

In the case of immunoassays, the hapten bound to a solid phase serves to separate off a complex to be determined from a reaction solution by binding with a substance specifically bindable with the hapten, for example an antibody directed against the hapten. Here, too, it is important that the hapten remains bound to the carrier since otherwise the results are falsified.

All the previously known processes for the binding of haptens to a matrix proved not to be optimal. The binding of the haptens to the matrix was not sufficiently strong so that when using the conditions necessary for the particular processes, the carrier bled, i.e. it gave off the hapten.

Another problem in the case of binding a hapten to a carrier is the fact that the hapten must be bound in such a manner that its active site is not blocked so that its activity is also not partly lost.

It is an object of the present invention to provide a process with which haptens can be fixed to a carrier without losing their activity and without being dissolved from the carrier when using the conditions necessary in the case of immunoassays or affinity chromatography.

Thus, according to the present invention, there is provided a process for the production of a polysaccharide matrix to which haptens are covalently bound, wherein polysaccharide-containing material is rendered alkaline, dried to a water content of less than 5% and then reacted in an anhydrous medium with a hapten containing at least one activated functional group.

Surprisingly, we have ascertained that, in the case of the use of the process steps according to the present invention, the hapten is, on the one hand, so strongly bound to the matrix that it is not dissolved off even in the case of the use of drastic conditions and, on the other hand, the binding of the hapten takes place in such a manner that it does not lose its activity.

The process according to the present invention serves for the production of a haptenized polysaccharide matrix. For this purpose, a polysaccharide-containing material is used. As polysaccharides, there are especially suitable the readily obtainable polysaccharides which are practically insoluble in water, such as agarose, dextran or cellulose. These polysaccharides can be admixed with other inert components. Cellulose is preferably used as polysaccharide. Examples of cellulose-containing materials which can be used include pure cellulose, sulphite wood pulp, viscose staple and/or cellulose acetate, as well as mixtures of these components. Furthermore, the material can be mixed with other fibres which are usually employed in such materials. Thus, for example, there can be used polyesters, nylon or polyacrylonitrile.

The properties of the polysaccharide-containing material can be varied according to the purpose of use. Thus, hydrophobicity, surface properties and the like can be adjusted by the use of appropriate polysaccharide derivatives. Differing hydrophobicity can be achieved, for example, by the use of cellulose acetate with differing degree of acetylation for the production of the matrix. Materials are preferably used which have a high proportion of polysaccharide.

The polysaccharide-containing material is first rendered alkaline. Due to the action of basic substances, at least a part of the hydroxyl groups of the polysaccharide are thereby converted into the active salt form. For the alkalization, there can be used, for example, aqueous solutions of alkali metal hydroxides or alcoholates dissolved in an organic solvent. For the alkalization, there are preferably used alkali metal hydroxides or alkali metal alcoholates dissolved in the corresponding alcohol. Aqueous sodium hydroxide solution or sodium methanolate dissolved in methanol are especially preferably used.

The alkali concentration is itself not critical but the optimum concentration depends upon the amount of hapten used. If the hapten is to be used in a large amount with regard to the polysaccharide material, then the amount of alkali should also be correspondingly greater and, vice versa, when using small amounts of hapten, it should be reduced. The optimum amounts used in a particular case can be ascertained by a few preliminary experiments. The alkalizing agent is preferably used in a concentration of 0.005 to 5 N, especially preferably of 0.01 to 1 N and particularly of 0.05 to 0.2 N.

Subsequent to the alkalisation, the polysaccharide-containing material is carefully dried to a residual water content of at most 5%. The material is preferably dried to such an extent that the water content is less than 2% by weight. Drying takes place in known manner, the drying conditions being such that the polysaccharide-containing material is not damaged.

If an alcoholate dissolved in an alcohol is used for the alkalization, then drying is not necessary.

The alkalized, dried, polysaccharide-containing material is then reacted with the hapten in an anhydrous medium. Therefore, the reaction preferably takes place in an anhydrous organic solvent, for example acetone, dimethyl formamide or dioxan.

Subsequently, washing is carried out with organic solvents and with an aqueous buffer solution with a pH of 6 to 8 and possibly again washed with water.

For the reaction with the polysaccharide-containing material, there can be used all haptens which have a functional group or into which a functional group can easily be introduced. As haptens, there are preferably used $T_3$, $T_4$, digoxin, diphenylhydantoin, folate and/or biotin.

The hapten is bound to the polysaccharide via an activated functional group. If the hapten used already has a functional group which is suitable for the binding, then this is activated and the reaction follows subsequently. If the hapten does not possess an appropriate functional group, then a functional group is introduced into the hapten by known methods. Appropriate functional groups for binding with the polysaccharide are, in particular, carboxyl, hydroxyl and amino groups and appropriate for the introduction of a functional group are especially carboxylic acids reactive in the $\omega$-position which are bound, for example, via oxime or amide formation or alkylation, on to the hapten.

The activation of the functional group also takes place according to known methods. The carboxyl group is thereby derivatised in such a manner that it can react easily with the $O^-$ groups of the polysaccharide-containing material. Thus, possibilities for the activation are described by K. Lübke, E. Schröder and G. Kloss in Chemie und Biochemie der Aminosäure, Peptide und Proteine I, pub. Georg Thieme Verlag, Stuttgart, 1975, pp. 136–137. In carrying out the process according to the present invention, preferred variants for the activation of the carboxyl group are the imidazolide and acid chloride methods, as well as the activated N-hydroxyester method with the use of N-hydroxyimides and the mixed carboxylic acid anhydride method. According to the present invention, an activated N-hydroxyester is especially preferably used in which case the hydroxysuccinimide ester is especially preferably employed.

If, as functional group, the hapten contains an amino group, then activation preferably takes place with bromoacetic acid chloride. For the activation of a hydroxyl group, there is preferably used a dicarboxylic acid possibly activated, for example, as the anhydride.

The activated hapten is reacted with the polysaccharide-containing material in an anhydrous medium. The amounts of components employed which are optimal in any particular case depend upon the nature and intended use of the material. A ratio of polysaccharide-containing material to hapten in the range of from $10^4$ to 0.1:1 has proved to be suitable, the ratio of polysaccharide-containing material to hapten preferably being from $10^3$ to 10:1.

The preferred concentrations are in the range of from $10^{-4}$ to 10 g./liter and especially preferably from $10^3$ to $10^{-1}$ g./liter.

The polysaccharide-containing material to which the hapten is covalently bound and produced according to the present invention is worked up in known manner, depending upon the intended use. For use in affinity chromatography, the material is preferably present in the form of spheroids or powder. For use in immunoassays, the polysaccharide-containing material is preferably used in the form of films, fleece or paper. It is now, on the one hand, possible to react the polysaccharide-containing material first with the activated hapten and subsequently to bring the haptenized material into the desired form. On the other hand, it is also possible first to bring the polysaccharide-containing material into the desired form and subsequently to react it with the activated hapten. Thus, for example, cellulose fibres can first be haptenized and then subsequently the fibres are worked up to give a fleece. On the other hand, spheroids can first be formed from the polysaccharide-containing material which are then subsequently haptenized.

The reaction of the alkalised and dried polysaccharide-containing material with the activated hapten preferably takes place in a device which comprises a winding core in a container for a reaction solution which has a tube, provided on its wall with a plurality of openings and closed on one end, for the reception of a winding of the material to be treated and two axial end plates for sealing off the axial ends of the winding and, by means of a circulating pump cycle, the reaction solution is passed from the container to the other end of the tube.

The end plates can thereby preferably be stressed against the axial ends of the winding.

In a preferred embodiment of the device, the reaction solution containing the activated hapten is now filled into the container. The alkalized and dried polysaccharide-containing material, which is present in the form of a strip, is then wound up on to the winding core and fixed with a gauze. The paper edge is sealed off by the end plates. The reaction solution is then passed by means of the circulating pump cycle from the container to the other end of the tube. The reaction solution thereby flows through the wound up material in all directions radially from the inside outwardly. It is an advantage of this device that only a small amount of organic solvent has to be used. Furthermore, the apparatus is very easy to handle and to clean.

With the process according to the present invention, using easily available materials, there can be produced a widely usable matrix on a production scale in a homogeneous and reproducible manner, which can be used not only for chromatography but also, for example, as a specific matrix or as a universal matrix in immunoassays. The haptenized matrix produced according to the present invention thereby serves as solid phase. This haptenized matrix produced according to the present invention can be used in two different variants for determination processes according to the immunoassay principle.

On the one hand, on the matrix can be bound a hapten which can bind quantitatively and specifically a conjugate of a substance to be determined and a labelled substance specifically bindable therewith. Thus, for example, $T_3$ or $T_4$ can be immobilised on the matrix and then a conjugate, which contains an antibody directed against $T_3$ or $T_4$, bound therewith.

Another process variant consists in that to the hapten is again bound a specifically bindable substance which in turn can react with derivatised conjugates of a substance to be determined and therewith bindable labelled substance. Thus, for example, biotin can be immobilized on the matrix and then an antibody conjugated with avidin is bound. Streptavidin or avidin specifically binding biotin can be bound to the immobilized biotin molecules. A matrix prepared in this manner can then be used as universal matrix and reacted with any biotinylated antibody or an otherwise specifically bindable biotinylated substance.

The following Examples are given for the purpose of illustrating the present invention, reference being made to FIG. 1 of the accompanying drawings, this Figure showing a device for carrying out the process according to the present invention.

It will be understood that the specification and examples are illustrative of the present invention and that other embodiments within the spirit and scope of the invention will suggest themselves to those skilled in the art.

FIG. 1 shows a container 1 for a reaction solution in which is present a winding core 3. The winding core 3 has, on one end 9, a closed tube 11 for the reception of a winding 13 of the material to be treated, the tube 11 having a plurality of openings 7. On the axial end faces of the winding 13 are arranged two axial end walls 15, 17 for sealing off which can be stressed against the axial end faces of the winding 13. Furthermore, the apparatus has a circulating pump cycle 19 which passes the reaction solution from the container 1 to the other end 21 of the tube 11.

EXAMPLE 1

25 m. of a cellulose-containing paper are treated in a paper impregnation apparatus by bath impregnation with 0.1 N sodium hydroxide solution. After the take up of the alkaline solution, the alkalized paper is dried on the paper impregnation apparatus by air circulation at 50° to 80° C.

Triiodothyronine ($T_3$) is used as hapten. The amino group of the $T_3$ is protected by a tert.butyloxycarbonyl radical (BOC) and the carboxyl group is activated by conversion into a hydroxysuccinimide ester. A solution is prepared of 25 mg. BOC-$T_3$-N-hydroxysuccinimide ester in 4 liters of acetone.

The esterification of the derivatives $T_3$ with the alkalized cellulose-containing paper is carried out in a reactor as is illustrated in FIG. 1 of the accompanying drawings. The alkalized paper on a paper roll machine is thereby bound thickly and compactly on the winding core of the reactor and fixed with a nylon gauze. The paper edge is sealed off by the snug screwing on of the sealing walls. The core wound with the alkalized paper is introduced into the reaction vessel which contains the reaction solution. The reaction solution is then pumped round with a flowthrough rate of 2.5 liters/minute with the pump via the pipes and flows through the paper in all directions radially from the inside outwardly.

After a reaction time of 1.5 hours at ambient temperature, the reaction solution is removed and 4 liters of acetone are pumped round at ambient temperature for 5 minutes for washing. Subsequently, washing is carried out for 10 minutes at ambient temperature with a buffer solution which contains 0.1 mole/liter phosphate buffer and 1% Tween 20 and has a pH of 7. This is followed by two further washings with this buffer in each case at 50° C. and for 10 minutes. Subsequently, washing is carried out with water for 5 minutes at ambient temperature.

The paper thus obtained is dehydrated in the reactor by pumping round 4 liters of acetone for 5 minutes. A final drying is then carried out on the paper impregnation apparatus at 50° C. with circulating air to a residual moisture content of 1.5 to 2%.

EXAMPLE 2

$T_4$ is bound as hapten to cellulose-containing paper. The process is carried out as described in Example 1 except that, instead of BOC-$T_3$-hydroxysuccinimide ester as reaction solution, there is used a solution which contains 100 mg. BOC-$T_4$-N-hydroxysuccinimide ester.

EXAMPLE 3

Figure 2:
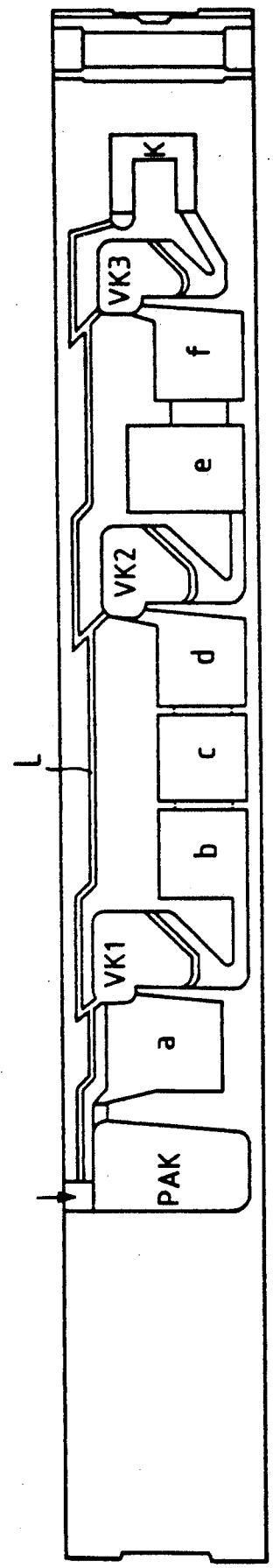

Determination of the binding capacity of a $T_3$ matrix with the use of an insert element according to FIG. 2 of the accompanying drawings in an apparatus according to European Patent Specifications Nos. 0,167,171 and 0,167,175.

Description of the insert element:

a:
  fleece of 40% linters 941, 50% polyamide and 10% Kuralon
  30 mmole/liter sodium phosphate dodecahydrate
  0.05% Genapol PF20 b:
  empty chamber (no fleece)

c:
  fleece of 20% linters 941, 30% viscose staple, 40% polyamide 8,2/4 and 10% Kuralon impregnated with a solution of
  38 mmole/liter disodium hydrogen phosphate dihydrate
  36 mmole/liter sodium dihydrogen phosphate monohydrate
  3.5 mmole/liter magnesium dipotassium ethylenediamine-tetraacetate dihydrate
  0.7% bovine serum albumin
  0.7% Crotein C
  0.035% anilinonaphthylsulphonic acid (ANS)
  0.01% Genapol PF 20.

d:
  fleece of 80% polyester and 20% viscose staple impregnated with a solution of 280 U/liter polyclonal antibody against $T_3$, coupled to $\beta$-galactosidase
  100 mmole/liter 4-(2-hydroxyethyl)-1-piperazineethanolsulphonic acid (HEPES), pH 7.25
  5 mmole/liter magnesium L-aspartate
  1% Crotein C
  The impregnated fleece is lyophilised for storage.

e:
  fleece analogous to Example 1 (matrix 9).

f:
  fleece of 20% linters, 30% viscose staple, 40% polyamide and 10% Kuralon impregnated with a solution of
  19 mmole/liter chlorophenyl red galactoside
  100 mmole/liter HEPES, pH 7.25
  10 mmole/liter boric acid.

Liquid Pipetting

56 μl. of a 0.9% by weight solution of sodium chloride are pipetted as sample into the sample application chamber. (PK).

Carrying out of the Reaction

When the sample is pipetted into the sample application chamber, the centrifuging programme begins. By the cooperation of gravity, capillary forces and centrifugal force, the sample solution is transported through the various reagent carriers to the cuvette. In order to control the chronological sequence of the reaction steps, there is used the centrifuging programme shown in the following Table 1. In this Table are given the step numbers, period of the particular centrifuging step in seconds, speed of rotation in r.p.m. and a description of the function of the step in question.

For the measurement (step 26), the solution is transported into the cuvette and the reaction is monitored absorption photometrically at 578 nm. The conjugate molecules which are not bound by the matrix (fleece e) could pass the matrix and there is now present in the cuvette a corresponding amount of enzyme. The measured colour increase per unit time (extinction/min., mE/min.) is thus a measure of the binding capacity of the matrix. The smaller is the measured colour increase per minute, the greater is the binding capacity of the matrix.

TABLE 1

| step | sec. | r.p.m. | Centrifuging programme |
|---|---|---|---|
| 1 | 60 | 100 | tempering of disposable with sample in PAK |
| 2 | 5 | 200 | sample on buffer fleece 1 in field a |
| 3 | 20 | 400 | elution of the buffer fleece |
| 4 | 15 | 3500 | |
| 5 | 45 | 600 | mixing and incubation in VK 1 |
| 6 | 40 | 0 | discharge of VK 1 |
| 7 | 5 | 100 | sample on buffer fleece 2 in field c |
| 8 | 25 | 250 | sample on conjugate fleece in field d |
| 9 | 15 | 3500 | elution of buffer fleece 1 and conjugate fleece |
| 10 | 140 | 600 | homogeneous reaction in VK 2 |
| 11 | 130 | 600 | |
| 12 | 60 | 0 | discharge of VK 2 |
| 13 | 5 | 100 | sample on matrix fleece in field e |
| 14 | 5 | 300 | matrix reaction |
| 15 | 120 | 100 | |
| 16 | 120 | 100 | |
| 17 | 2 | 400 | centrifuging off of the matrix |
| 18 | 2 | 600 | separation of bound free conjugate |
| 19 | 2 | 800 | sample on substrate fleece in field f |
| 20 | 2 | 1200 | thereby start of the indicator reaction |
| 21 | 0 | 100 | start timer |
| 22 | 10 | 3500 | centrifuging off of the matrix and substrate fleece |
| 23 | 15 | 0 | discharge of VK 3 |
| 24 | 2 | 100 | |
| 25 | 2 | 300 | filling of the cuvette |
| 26 | 60 | 720 | measurement (wavelength λ = 578 nm) |
| 27 | 3600 | 3600 | end |

FIG. 2 shows a disposable such as is used for carrying out the process described in the above Example 3. In this Figure:

PAK=sample application chamber
VK1, VK2 and VK3=valve chambers
K=measurement cuvette
L=ventilation canal The individual fleece and chambers are illustrated schematically. Bridges which produce the contact between the individual chambers and fleece thereby mean, in each case, connections by means of which the liquid to be investigated can be further transported.

EXAMPLE 4

In an alternative process, the binding capacity of a $T_3$ matrix was determined. For this purpose, there were used the following reagents:

a) buffer:
  38 mmole/liter disodium hydrogen phosphate dihydrate
  36 mmole/liter sodium dihydrogen phosphate monohydrate
  3.5 mmole/liter magnesium dipotassium ethylenediamine-tetraacetate dihydrate
  0.7% bovine serum albumin
  0.7% Crotein C
  0.035% anilinonaphthylsulphonic acid (ANS)
  0.01% Genapol PF 20
b) chlorophenol red galactoside solution (19 mMole/liter) in buffer (100 mmole/liter HEPES, pH 7.25; 10 mmole/liter boric acid)
c) anti-$T_3$-antibody-$\beta$-Gal conjugate solution of a conjugate of polyclonal antibody against $T_3$ with $\beta$-galactosidase ($\beta$-Gal) ($\beta$-galactosidase activity: 280 U/liter in buffer a).

For carrying out the test, the sample (0.9% by weight sodium chloride solution) was diluted in a ratio of 1:10 with anti-$T_3$-antibody-$\beta$-Gal conjugate solution. 50 μl. of this mixture were soaked up by 10 mg. of the $T_3$-carrying paper (produced according to Example 1) and incubated for 10 minutes at 37° C. For the removal of unbound conjugate, the paper was washed three times with, in each case, 100 μl. of buffer, the washing solution thereby being removed after each washing step by centrifuging. Subsequently, the paper was impregnated with 50 μl. chlorophenol red galactoside solution. After incubating for 5 minutes at 37° C., the coloured material solution formed was separated off from the paper by centrifuging and measured at a wavelength of 578 nm in a microcuvette with a filling volume of 27 μl. and a layer thickness of 0.6 cm. The measured extinction is inversely proportional to the binding capacity of the sample.

EXAMPLE 5

Biotin was bound as hapten to cellulose-containing paper. The process was carried out in the manner described in Example 1. Instead of BOC-$T_3$-hydroxysuccinimide ester, as reaction solution there was used a solution which contained 200 mg. biotin-N-hydroxysuccinimide ester.

EXAMPLE 6

A cellulose-containing paper derivatised with $T_3$ was produced. The process was carried out in the manner described in Example 1. However, a different $T_3$ derivative was used. For this purpose, $T_3$ was derivatised with bromoacetyl chloride to give $BrCH_2CO$-$T_3$. 5 mg. $BrCH_2CO$-$T_3$ in 125 ml. dioxan were applied to 2 g. of alkalized paper and shaken overnight at ambient temperature. Subsequently, washing was carried out twice with, in each case, 50 ml. dioxan, acetone and water. The so treated paper was treated for 12 hours with 2.5 liters 20 mM phosphate buffer (pH 8) in a column with slow rinsing through, subsequently treated with 50 ml. of water and 50 ml. acetone and dried in a vacuum.

EXAMPLE 7

The extent to which the binding capacity of the cellulose for a hapten is influenced by the drying was investigated. For this purpose, alkalized cellulose on which $T_3$ was immobilised was dried under differing conditions and subsequently reacted with BOC-$T_3$-N-hydroxysuccinimide ester in the manner described in Example 1, the results obtained being given in the following Table 2. The binding capacity is thereby inversely proportional to the extinction value (determination as described in Example 3).

TABLE 2

| drying | extinction value for $T_3$ (mE/min.) |
|---|---|
| moist paper | 550 |
| dried with acetone to about 13% water content | 450 |
| dried for 2 hours at 25° C. in a circulating air drying cabinet to about 8% water content | 212 |
| dried overnight in a desiccator to 1% water content | 75 |

EXAMPLE 8

The influence of the water content of the reaction medium on the binding capacity was tested. For this purpose, 0.33 mg. BOC-$T_3$-N-hydroxysuccinimide ester, per g. of paper, dissolved in an amount of 2 mg./liter acetone, was coupled to the paper in the manner described in Example 3. The determination of the binding capacity took place in the manner described in Example 4. To one paper which, after washing and drying in the manner described in Example 1, was additionally dried in a vacuum drying cabinet at 50° C./10-2 mm.Hg, was added, for testing the influence of the water content, the amounts of water set out in the following Table 3. The statement of percentage means by weight of solvent which represents the reaction medium. The results obtained are also set out in the following Table 3.

TABLE 3

| % water | binding capacity (mE/min.) |
|---|---|
| 0.2 | 47 |
| 0.5 | 48 |
| 1.0 | 65 |
| 10 | 1298 |

EXAMPLE 9

In the manner described in Example 1, a paper was prepared to which diphenylhydantoin was coupled. For this purpose, 1 mg. diphenylhydantoin valeric acid N-hydroxysuccinimide ester was used per g. of paper. A reaction solution was prepared which contains 6 mg. diphenylhydantoin valeric acid succinimide ester per liter of acetone.

What is claimed is:

1. A method for the production of a polysaccharide matrix to which a hapten is covalently bound for use in affinity chromatography or immunoassay comprising
   rendering a polysaccharide-containing material of the matrix alkaline,
   drying the polysaccharide-containing material of the matrix to a water content of less than 5%, reacting the dried polysaccharide-containing material of the matrix with an activated hapten comprising at least one activated carboxyl, amino or hydroxyl functional group whereby the hapten is bound to the polysaccharide in an anhydrous organic solvent in a range of polysaccharide:hapten of $10^4$ to 0.1:1 to form a polysaccharide matrix so that the hapten retains its activity and is so bound to the matrix that it is not removed in solution or during reaction, and washing the reacted matrix with an organic solvent and an aqueous buffer of pH 6-8.

2. The method of claim 1 wherein the polysaccharide-containing material which is rendered alkaline is a cellulose containing material.

3. The method of claim 2 wherein the cellulose containing material rendered alkaline is cellulose, sulphite wood pulp, viscose stable, cellulose acetate or a mixture thereof.

4. The method of claim 1 further comprising rendering the polysaccharide-containing material alkaline by treatment with aqueous 0.005-5 N alkali metal hydroxide.

5. The method of claim 1 further comprising rendering the polysaccharide-containing material alkaline by treatment with an alkali metal alcoholate.

6. The method of claim 1 further comprising drying the polysaccharide-containing material of the matrix to a water content of less than 2%.

7. The method of claim 1 further comprising reacting the polysaccharide-containing material of the matrix with a hapten comprising an activated carboxyl group wherein the activation of the carboxyl group takes place with an acid chloride, a hydroxyimide, a carbodiimide, an anhydride or an imidazolide.

8. The method of claim 1 further comprising reacting the polysaccharide-containing material of the matrix with an activated hapten selected from the group consisting of $T_3$, $T_4$, digoxin, diphenylhydrantoin, folate, biotin and a derivative thereof.

9. A polysaccharide matrix composition comprising a polysaccharide-containing material with a water content of less than 5% and a hapten bound covalently thereto via an activated carboxyl, hydroxyl or amino group on the hapten and wherein the hapten retains its activity and is so bound to the matrix that it is not removed while in solution or during reaction.

10. The polysaccharide matrix of claim 9 wherein the polysaccharide-containing material is selected from the group consisting of cellulose, sulphite wood pulp, viscose staple, celulose acetate and a mixture thereof.

11. The polysaccharide matrix of claim 9 comprising a polysaccharide-containing material with a water content of less than 2%.

12. The composition of claim 9 wherein the hapten is selected from the group consisting of $T_3$, $T_4$, digoxin, diphenylhydantoin, folate, biotin and a derivative thereof.

* * * * *